(12) United States Patent
Akbarshahi (10) Patent No.: US 12,220,318 B2
(45) Date of Patent: Feb. 11, 2025

(54) HIP ARTHROPLASTY DYNAMIC OPTIMIZATION SYSTEM

(71) Applicant: Zimmer Biomet Pty Ltd, Belrose (AU)

(72) Inventor: Massoud Akbarshahi, Belrose (AU)

(73) Assignee: Zimmer Biomet Pty Ltd, Belrose (AU)

( * ) Notice: Subject to any disclaimer, the term of this patent is extended or adjusted under 35 U.S.C. 154(b) by 390 days.

(21) Appl. No.: 17/738,745

(22) Filed: May 6, 2022

(65) Prior Publication Data

US 2022/0354652 A1 Nov. 10, 2022

Related U.S. Application Data

(60) Provisional application No. 63/185,031, filed on May 6, 2021.

(51) Int. Cl.
| | | |
|---|---|---|
| *A61F 2/30* | (2006.01) | |
| *A61B 5/11* | (2006.01) | |
| *A61B 34/10* | (2016.01) | |
| *A61F 2/32* | (2006.01) | |

(52) U.S. Cl.
CPC .......... *A61F 2/30942* (2013.01); *A61B 5/11* (2013.01); *A61F 2/32* (2013.01); *A61B 2034/104* (2016.02); *A61B 2034/105* (2016.02); *A61F 2002/30948* (2013.01); *A61F 2240/008* (2013.01)

(58) Field of Classification Search
USPC ...................................................... 382/128
See application file for complete search history.

(56) References Cited

U.S. PATENT DOCUMENTS

| | | |
|---|---|---|
| 8,177,850 B2 | 5/2012 | Rudan et al. |
| 10,595,943 B2 | 3/2020 | Barsoum et al. |
| 2015/0223939 A1 | 8/2015 | Miles et al. |
| 2019/0151098 A1 | 5/2019 | Van Der Wal et al. |
| 2019/0180466 A1 | 6/2019 | Tao |
| 2021/0059838 A1* | 3/2021 | Bodner ................ A61B 5/1121 |
| 2022/0117663 A1* | 4/2022 | McGuan .................. G06N 5/01 |

FOREIGN PATENT DOCUMENTS

WO WO-2022234341 A1 11/2022

OTHER PUBLICATIONS

"International Application Serial No. PCT IB2022 000266, International Search Report mailed Sep. 28, 2022", 3 pgs.
"International Application Serial No. PCT IB2022 000266, Written Opinion mailed Sep. 28, 2022", 4 pgs.
"International Application Serial No. PCT/IB2022/000266, International Preliminary Report on Patentability mailed Oct. 24, 2023", 5 pgs.

* cited by examiner

*Primary Examiner* — Darryl V Dottin
(74) *Attorney, Agent, or Firm* — SCHWEGMAN LUNDBERG & WOESSNER, P.A.

(57) ABSTRACT

Various embodiments disclosed relate to a method for producing an implant model and associated systems. The method can include receiving patient specific data, producing a preliminary implant model based on the received patient specific data, running a simulation on the preliminary implant model to produce a revised implant model with a range of motion zone using the patient specific kinematics, optimizing the preliminary implant model with a dynamic simulation to determine a cup anteversion angle, analyzing the revised implant model for spino-pelvic risk, and outputting the implant model.

20 Claims, 5 Drawing Sheets

HIP ARTHROPLASTY DYNAMIC OPTIMIZATION SYSTEM

CLAIM OF PRIORITY

This application claims the benefit of U.S. Provisional Patent Application Ser. No. 63/185,031, filed on May 6, 2021, the benefit of priority of which is claimed hereby, and which is incorporated by reference herein in its entirety.

TECHNICAL FIELD

The present subject matter relates to orthopedic procedures and, more particularly, to systems and methods that can aid in performing hip arthroplasty.

BACKGROUND

The hip joint is a ball and socket joint formed by articulation between the head of the femur and the pelvic acetabulum. The hip joint connects the legs to the pelvic girdle, and provide stability and weight bearing properties. In the hip joint, the acetabulum is a cup-like depression in the pelvis having a fibrocartilaginous collar. The head of the femur can fit in the acetabulum. Both components can be covered in articular cartilage. The hip joint can be subject to degenerative changes, such as those caused by arthritis.

Arthroplasty involves replacement, remodeling, or realignment of a musculoskeletal joint to restore function of the joint or relieve pain, for example after arthritis or other types of trauma. Hip arthroplasty, or total hip replacement, can be used, for example, to treat joint failure caused by osteoarthritis, rheumatoid arthritis, other variants of arthritis, some hip fractures or breaks, certain types of bone tumors, and other conditions. Hip arthroplasty can be used to relieve pain and improve hip function. In hip arthroplasty, the hip joint is surgically replaced by a prosthetic implant, such as a hip prosthesis. A total hip replacement includes replacing both the acetabulum and the femoral head.

When it has been determined that a patient should have a hip replacement, the medical team can select the type and design of hip prosthesis. For example, surgeons can use preoperative planning, display devices, and imaging, to improve diagnoses and surgical outcomes.

SUMMARY OF THE DISCLOSURE

Disclosed is a method and system for choosing and optimizing a patient hip implant based on patient specific data, such as patient desired daily activities post-implant. An example method collects patient-specific imaging data to choose an appropriate model with the best size implant and stem anteversion angle, and applies patient-specific hip kinematics to the model. The kinematics can include input for desired daily and recreational activities, such as sports, based on a patient profile. Then, the patient-specific implant model can be optimized, for example the optimal cup anteversion can be determined to maximize range of motion without impingement. Spino-pelvic kinematic analysis of the model can be performed to determine safety and interaction of the hip implant with the pelvis/spine. Based on these inputs, a specific hip implant model and prescription can be produced for the patient. The doctor can, based on the produced patient-specific implant model, have realistic discussions with the patient of their range of motion, mobility, and activity level post-implant.

In preparation for hip replacement surgery, the components of the implant can be matched with the biology of the patient in an effort to maintain or restore a natural range of motion of a healthy hip joint. When a hip replacement is planned, the surgical team can put together a preoperative plan for the patient, including a model of a recommended implant. Such an implant model can be analyzed to allow for determination of a future patient range of motion. However, each patient not only has varying anatomy, but may also have varying desires for levels of physical activity post-implant, and restoring a full range of motion can be challenging.

Typical approaches to implant planning have used one-dimensional or isolated pelvic motion during their determinations of implant modeling and range of motion. In some cases, other approaches have only looked at an implant femur or an implant cup. Leveraging such a kinematic envelope in modeling and production of an implant could include a patient's range of motion.

By comparison, other approaches have used pathology-affected kinematic data regarding the implant only on two positions: sitting and standing. Modeling the implant with kinematics representing a more wholistic approach to patient movement can help produce a better simulation and implant, help manage patient expectations for life with the implant, and aid the surgeon in analyzing any pelvic risk associated with the implant.

Discussed herein, the proposed methods and system can allow for incorporation of patient-specific anatomy data and full kinematic envelope into the production of the implant model to produce a preferred range of motion. The implant model can be optimized based in part on the patient specific kinematics to allow for a prediction of the range of motion for the implant without impingement. This can allow for production of a patient specific implant model and preoperative plan that is suited to the patient's movement desires post-implant and closer to a natural range of motion for the hip joint. Additionally, this can allow for the surgical team to produce realistic expectations for the patient in regard to range of motion after the implant is applied, and aid in managing the patient's overall expectations when dual mobility is prescribed.

While the discussion herein relates specifically to hip replacement procedures, discussion of the following systems, devices, methods, and instruments can also be applicable for use in other joint replacement procedures, such as shoulder arthroplasty or knee arthroplasty.

In an example, a method for producing an implant model can include receiving patient specific data comprising patient anatomy information and patient specific kinematics; producing a preliminary implant model based on the received patient specific data; running, using processing circuitry, a simulation on the preliminary implant model to produce a revised implant model with a range of motion zone using the patient specific kinematics; optimizing the preliminary implant model with a dynamic simulation to determine a cup anteversion angle and a revised impingement free range of motion zone; analyzing the revised implant model for spino-pelvic risk using spino-pelvic kinematics, and adjusting the implant model based on the spino-pelvic risk and kinematic behavior; and outputting the implant model for display on a user interface.

In an example, a method for providing implant parameter data can include receiving patient specific data comprising patient anatomy information and normative patient matched kinematics; determining an implant size and a stem anteversion angle based on the patient anatomy information;

producing a range of motion for the patient based on the determined implant size and the patient kinematics, wherein the range of motion is maximized and impingement free; constructing a preliminary implant model based on the range of motion; analyzing spino-pelvic risk of damage due to the preliminary implant model and revising the preliminary implant model based on the spino-pelvic risk; and outputting the revised preliminary implant model for display on a user interface.

In an example, a system can include processing circuitry; and memory, the memory including instructions for producing an implant model, which when executed by the processing circuitry, causes the processing circuitry to: receive patient specific data comprising patient anatomy information and patient specific kinematics; produce a preliminary implant model based on the received patient specific data; run a simulation on the preliminary implant model to produce a revised implant model with a range of motion zone using the patient specific kinematics; optimize the preliminary implant model with a dynamic simulation to determine a cup anteversion angle and a revised impingement free range of motion zone; analyze the revised implant model for spino-pelvic risk using spino-pelvic kinematics, and adjusting the implant model based on the spino-pelvic risk; and output the implant model for display on a user interface.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure describes, among other things, a method and systems for producing an implant model for use in a preoperative plan. The implant model can be produced, for example, using patient specific kinematics to produce a range of motion specific to that patient's desired activity level. The implant model can additionally be size and shaped for the patient, and optimized through a dynamic simulation thereof.

Among many benefits, the proposed methods and system leveraging 3-D modeling and kinematic testing of the implant can allow for avoidance of impingement of the implant, and lower the risk of the patient having a dislocation once the implant is applied.

The methods and systems discussed herein can allow for a surgeon to incorporate patient kinematics envelope data, such as determining whether an implant will be used during sports, a particular job that is physically demanding, whether the patient will be bending or kneeling frequently, and other specific intended used for the implant. The patient specific profile can allow for adjustments in prescription angles for various portions of the implant and help the surgeon identify specific risks for the patient. This can aid in managing patient expectations, and avoid potential dislocation or impingement of the implant.

Figure 1A:
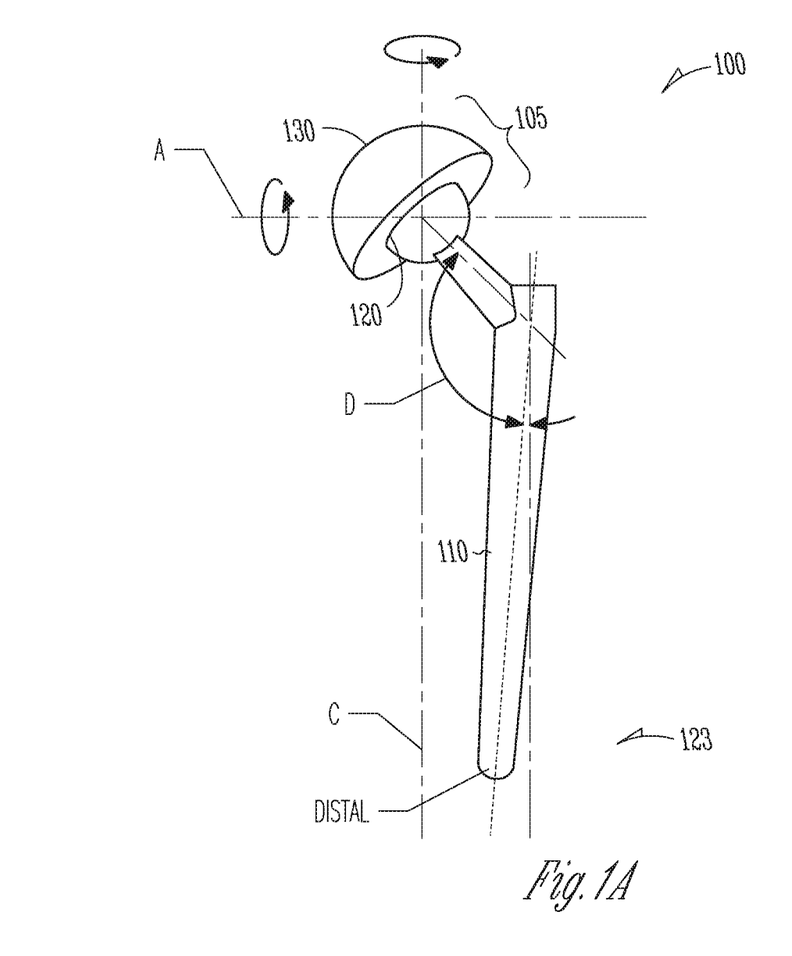
FIGS. 1A-1B depict perspective views of an example three dimensional model of a hip implant.
Figure 1B:
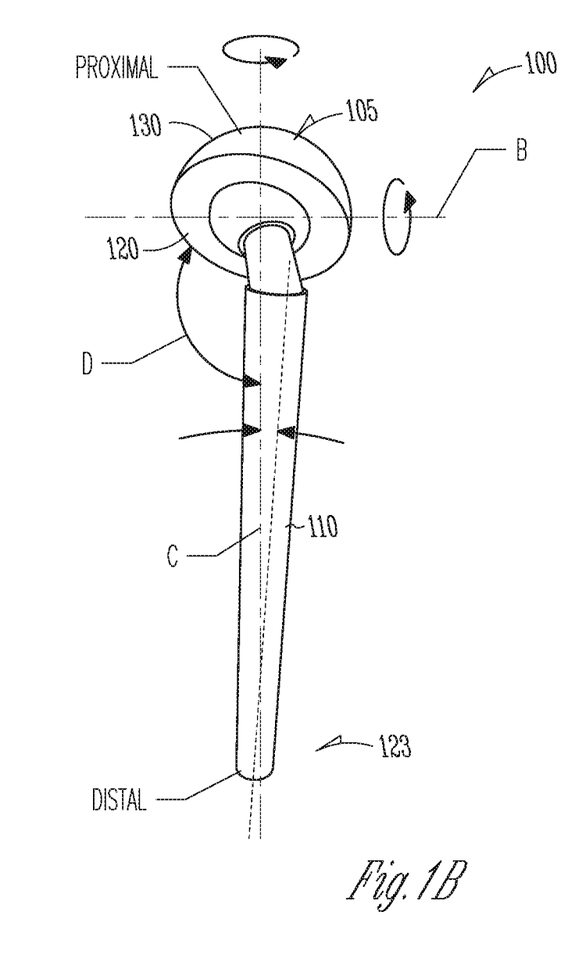

FIGS. 1A and 1B depict views of a hip model 100 that can include a stem 110, head 120, and cup 130. FIG. 1A depicts an anterior-posterior view, while FIG. 1B depicts a lateral view, of a three-dimensional computer generated model 100 of an implant for use in a hip arthroplasty. The model 100 can include axes A, B, and C, and angle D. The model 100 can be produced and tested, for example, with the system and methods described below with reference to FIGS. 2 and 3A-3B. The model 100 can be adjusted to allow for a range of motion (ROM) specified to the patient himself or herself. The production of model 100 can leverage a full kinematic envelope tailored to the patient's desired activities.

Orthopedic implants can include both a body segment 105, that replaces a joint (for example, head 120 and cup 130), and an intramedullary stem 110, that helps to fix the implant to the bone canal of the targeted bone. In model 100, the stem 110 can extend from the head 120. The stem 110 can be sized, shaped, or arranged for insertion in the femur of the patient during implementation. The intramedullary stem 110 can have a small cross-section so that the intramedullary stem 110 fits into the targeted femur canal.

Body segment 105 can support the intramedullary stem 110, such that the intramedullary stem 110 extends outwards from the body segment 105. Both the body segment 105 and the intramedullary stem 110 can extend into the bone when applied. In some cases, a head 120 can extend from the body segment 105 opposite the intramedullary stem 110. The head 120 can be a variety of shapes, such as a rounded or plate portion shaped, sized, or arranged to replace, reinforce, or supplement the femoral head. The body segment 105 can be used in a system including an acetabular cup, liner, or other implant component, that is implantable within a patient's acetabulum. In an example, the body segment 105 can include a prosthetic femoral head configured for articulation with a prosthetic acetabular cup. The body segment 105 can be a standard size or tailored to the specific patient based on measurements derived from medical images of the patient's joint.

The body segment 105 of the implant based on the model 100 can include a bone on-growth or in-growth material, or have a bone on-growth or in-growth feature, such as a raised splined surface, a roughened surface, metallic beads, a grit blasted surface, a porous surface, or a hydroxyapatite coating, or combinations thereof. For example, Trabecular Metal® a highly porous biomaterial made from elemental tantalum with structural, functional, and physiological properties similar to that of bone, can be used. All or a portion of the body segment 105 can be formed from a bone on-growth or in-growth material, or the material can be applied as an external coating.

The intramedullary stem 110 can extend from the body segment 105 and be used to secure the implant based on the model 100 in the body. The intramedullary stem 110 can be formed integrally or monolithically with the body segment 105. Alternatively, the intramedullary stem 110 can be formed as a separate element that is attachable to the body segment 105. The distal end 123 can be adapted to be inserted into a patient's intramedullary canal, and can help to guide insertion of all or a portion of the intramedullary stem 110 into the intramedullary canal. The distal end 123 can be flat, rounded, bullet-nosed, or other shapes as desired for insertion into the intramedullary canal. These shapes can allow for the distal end to be easily inserted into the canal, and minimize interference with and trauma to the surrounding bone. The intramedullary stem can optionally include one or more connection portions extending from the stem, such as a tapered or screw connection. In some cases, the intramedullary stem can include one or more tapered regions, such as to allow for a closer fit to the intramedullary canal during insertion. The intramedullary stem 110 can be straight or curved, such that it substantially matches the curvature of the anatomy of the patient to which it is being applied.

The body segment can include both the head 120 and the cup 130. The head 120 extend from the stem 110 towards the cup 130. The head 120 can fit into and allow movement relative the cup 130, which can imitate the acetabulum. In some cases, the head 120 can allow for dual mobility. The cup 130 can be likewise fitted to the head 120. The sizing of the stem 110, head 120, and the stem 110 can be produced using patient imaging and patient specific measurements, as discussed below.

Under normal circumstances, the hip joint can move in multiple directions, allowing hip flexion, extension, hyperextension, and abduction. Flexion can include movement that decreases the angle of the joint, bends the joint, or bring the bones of the joint closer together. Extension can include movement that straightens or opens the joint. Hyperextension can include extending the joint beyond the neutral anatomical position. Abduction can include movement of the leg away from the midline of the body.

In FIGS. 1A and 1B, flexion and extension can occur along the medial lateral line (axis A), while abduction and adduction can occur along the axis B. Internal and external rotation of the hip joint can occur around the axis C. Angle D can indicate the angle between the body 105 of the implant model 100 and the stem 110.

During the methods described below, an implant model, such as model 100, can be used as a three-dimensional computer generated model to test these various types of movement on the planned implant, and movement of these various types can be tested on the model. This can help the surgeon obtain a clearer picture of the range of motion of the planned implant, and as needed, adjust the planned implant for the patient's specific purposes and desires.

Range of motion (ROM) is the full potential of movement of a joint, measured in degrees of a circle. Active joint movement, passive joint movement, and combinations thereof can contribute to the ROM. In a hip, the normal ROM can be about 0 to 125 degrees for hip flexion, about 115 to 0 degrees for hip extension, about 0 to 15 degrees for hyperextension, and about 0 to 45 degrees for hip abduction.

In a hip arthroplasty, an implant model 100 can be used to optimize the actual implant used in the procedure. Goals of hip arthroplasty include relief of pain and restoration of a stable hip joint. The range of motion of an implant can depend on the implantation parameters, including cup anteversion and inclination, step antetorsion, and cup containment. Additionally, head-to-neck ratio in the implant, neck design, stem-neck angle, cup opening plane design, and offset of the implant model, can affect the range of motion of the implant.

The model 100 shown in FIG. 1 can be tested, adjusted, and optimized along the ROM according to the patient's specific desired kinematics envelope, including motion such as flexion, extension, and abduction. During the course of testing and analysis of the implant model 100, parameters such as including cup anteversion and inclination, stem antetorsion, cup containment, head-to-neck ratio in the implant, neck design, stem-neck angle, cup opening plane design, offset of the implant model, and implant sitting height can be adjusted at various points in the process. Thus, the implant model 100 can be produced for use, for example, in a preoperative plan prior to surgery. The implant model 100 can be used to address patient expectations regarding an upcoming hip replacement.

Figure 2:
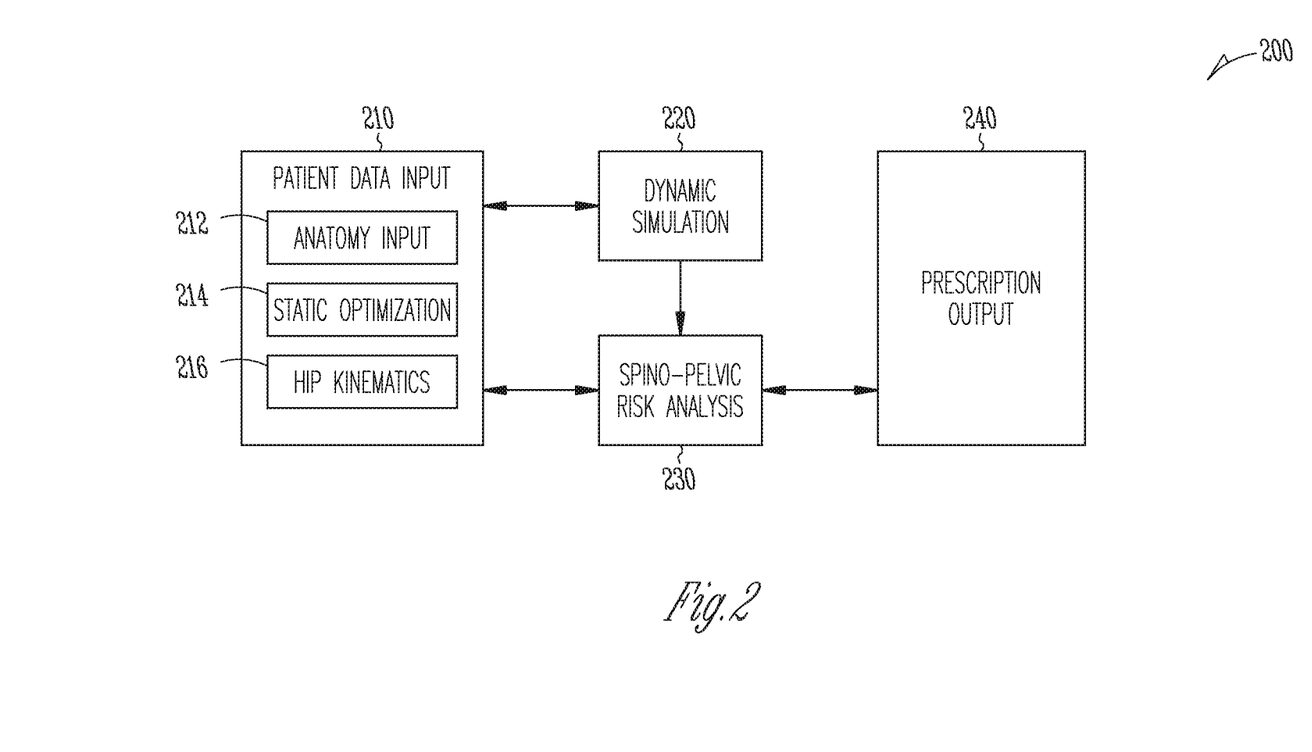
FIG. 2 is a schematic diagram of a system for hip implant optimization in an example.

FIG. 2 is a schematic diagram of a system 200 for hip implant optimization. The system 200 can include a patient data input platform 210 with an anatomy input 212, static optimization application 214, and hip kinematics application 216, a dynamic simulation 220, a spino-pelvic risk analysis application 230, and a prescription output application 240.

The system 200 can be used, for example, to execute a method for producing an implant model. Such a method can include, for example, receiving patient specific data, including patient anatomy information and patient specific kinematics; producing a preliminary implant model based on the received patient specific data; running a simulation on the preliminary implant model to produce a revised implant model and a range of motion zone based on the patient specific kinematics; optimizing the preliminary implant model with a dynamic simulation to determine a cup anteversion angle and a revised impingement free range of motion zone; analyzing the revised implant model for spino-pelvic risk using spino-pelvic kinematics, and adjusting the implant model based on the spino-pelvic risk; and outputting the implant model for display on a user interface. Example methods are discussed in more detail with reference to FIGS. 3A-3B below.

In the system 200, the patient data input platform 210 can be a program, application, or system configured to take in patient specific data and/or normative patient matched data for use in production of an implant model and preoperative plan. The patient data input platform 210 can include, for example, an anatomy input 212, a static optimization application 214, a hip kinematics application 216, or combinations thereof.

The patient data input platform 210 can receive the patient anatomy data from the anatomy input 212 and apply it in the static optimization application 214 to produce a preliminary implant model with a standard size stem, cup, and anteversion angle. The patient data input platform 210 can additionally receive patient specific kinematics data at the hip kinematics application 216, including information related to patient specific desired daily activities for the implant. This kinematics information can be applied to the statically optimized preliminary implant model to produce a patient-specific preliminary implant model for further testing.

The anatomy input 212 can be configured to receive patient imaging data, such as x-ray, MR, CT scans, or other data showing images of the patient hip desiring replacement. In some cases, the patient data can include two dimensional data. In some cases, the patient data can include three-dimensional data. In an example, two dimensional data can be converted to produce a three-dimensional model of the patient anatomy, such as the patient anatomy of the pelvis and femur.

Information from the anatomy input 212 can include numerical ranges of pelvis and femur size. For example, the appropriate cup size for the patient can be determined from the anatomy input. Similarly, the stem size and offset appropriate for the patient can be determined from the imaging data. The specific sizing, type, and brand of implant components can be selected here as preliminary components for the implant model. Once a preliminary implant size has been determined, static optimization of the anteversion angle can be done at static optimization application 214.

The static optimization application 214 can be used to determine the appropriate cup and stem size, and the appropriate stem anteversion angle. First, once the imaging data from the anatomy input 212 has been received, the static optimization application 214 can match the incoming patient specific anatomy data to a generic cup and stem size. The static optimization application 214 can used this information to produce a three dimensional model of the implant to begin testing.

After the appropriate cup and stem size have been selected, the static optimization application 214 can use the three-dimensional model (such as model 100) produced based on the anatomy input 212 and appropriate sizing to test the planned implant, and specifically determine an appropriate stem anteversion angle. The anteversion angle refers to the orientation of the femoral neck relative the condyles at the knee. Naturally, the femoral neck is oriented anteriorly. Femoral anteversion averages are naturally between about 8 to 14 degrees in adults. Reversed, or posterior orientation of the femoral neck can be referred to as femoral retroversion, and is preferably avoided with the implant model. Leg length and offset can also be taken into account.

An inappropriate or undesired anteversion angle can cause impingement of the cup and stem, which can cause dislocation, accelerated wear, and pain in patients with hip implants. An accurate stem and cup anteversion angle can allow for mating of the femoral head in the cup without impingement of the two components throughout various body positions. The total anteversion angle can include both the stem and cup anteversion angles. The total anteversion angle can be about 25.0 to about 45.0 degrees in accurate hip joints (or about 29.0 to abut 34.0 degrees). Mathematical models can be used to confirm the combined anteversion angle desired to prevent impingement.

In the static optimization application 214, the stem anteversion angle can be optimized. The stem anteversion angle can be about 9.0 to about 14.0 degrees (or about 8.0 to about 13.0 degrees). A stem anteversion angle can have a stable press fit to obtain bone fixation. A stable press fit means the stem can adapt to the femoral bone geometry. Femoral bone geometry can vary patient to patient. The total range of stem anteversion can range from about 15 degrees (retroversion) to about 30 degrees (anteversion). A range of about 15 degrees to about 30 degrees can allow for anteversion of the femoral stem.

During testing of the implant model at the static optimization application 214, portions of the three-dimensional model can be moved relative each other, such as in single or combined movements. Static optimization of the implant model stem anteversion angle can be produced by keeping one component of the preliminary implant model steady and moving the other component relative that component.

For example, the preliminary stem size and type can be selected. The stem can then be fixed in a particular location. The selected cup can be placed in an initial positions, according to standard literature. The orientation of the cup relative the stem can be changed bit by bit to allow optimization of the angel of the stem relative the cup to provide the appropriate cup anteversion for the implant model.

In some cases, to determine the appropriate anteversion stem angle, a surgeon estimated angle can be applied to the three-dimensional model. The stem anteversion angle can then be measured by the computer. These movements of the implant model can be recorded and analyzed as desired. Movements of the model during testing can be along physiological planes.

After static optimization is used to produce the appropriately sized stem, cup, and anteversion angle, a kinematics envelope can be applied to the preliminary implant model to further refine the model itself.

The hip kinematics application 216 can be configured to receive both the preliminary implant model from the static optimization application 214 and a patient specific kinematics envelope. The hip kinematics application 216 can apply the kinematics envelope to the preliminary implant model to further refine the model and surgical plan. The kinematics can be, for example, normative kinematics, matched specifically to the patient, such as matched to the patient age, status, or mobility.

The use of a kinematics envelope can test movement solutions for the entire range of motion of the implant model. The kinematics envelope of motion for a patient can be defined by multiple angles, such as passive ranges of motion from daily activities. The kinematics envelope can include information on typical and patient desired ranges for flexion, extension, abduction, rotation, and other types of movement. In some cases, particular movements can potentially create dislocation.

The average kinematics for desired daily and recreational activities can be included in the kinematics envelope specific to the patient. For example, daily activities and associated ranges of motion, such as sitting, standing, and walking can be included in the kinematics information. Similarly, patient specific activities can be included in the patient kinematic envelope, such as praying, kneeling, tennis, surfing, yoga, running, or other activities. A given number of daily activities, based on the patient preferences and profile, can be selected for association with the implant model.

Each of these daily activities can be selected, and each daily activity can include a range of motion. For example, a daily activity such as combing or brushing hair can be selected, which can include a predetermined approximate range of motion. Other daily activities can also be used, such as driving a car, stacking dishes on shelves, and opening a door. In some example, more than one daily activity and its range of motion can be selected.

For a specific daily activity, the range of motion of the preliminary implant model can be compared to the desired range of motion for that daily activity. Such a range of motion can be represented, for example, by a two or three dimensional graphical representation of a range of motion associates with that activity. Such information can be pulled from a database or conventional kinematics information regarding a range of motion desired for that activity. The hip kinematics application 216 can determine if the range of motion of the preliminary implant model is within an acceptable range of motion for that daily activity. In some cases, the comparison of the desired range of motion for the daily activity can be done prior to producing the preliminary model.

If the range of motion of the preliminary implant is successfully within the desired range of motion for the activity, the system can move on to test another daily activity, or finalize the dynamic simulation and send the revised preliminary implant model to the dynamic simulation 220 for further analysis. In some cases, a user, such as the surgeon or healthcare professional, can be prompted by the system to confirm that the range of motion is acceptable for this particular daily activity based on a recommendation from the system, prior to moving forward.

In some cases, particular daily activities can be weighed against each other. For example, the daily activity of walking can be placed at a higher priority than recreational activities such as sports. In this case, the kinematics application 216 can first test and adjust the implant model based on the walking range of motion, and subsequently test recreational activities such as sports (e.g., while staying within ranges or parameters established for the walking range of motion).

In some cases, the desired range of motion of the preliminary implant can be determined from an expected interaction between the virtual cup, head, and stem of the preliminary implant model. The expected interaction of these components can be modeled using several techniques, discussed in depth below. For example, the virtual head and stem can be rotated relative the cup. As the stem is moved, collisions, angles of impingement, or other problematic movements can be determined.

In some examples, the range of motion can be determined based on fit analysis. For example, data such as the thickness, offset, and placement of each insert can be compared to data from previous models and/or patients to determine an anticipated range of motion.

In some cases, the patient profiles can be stored in a database connected to the system 200. In this case, the patient profiles optionally already have kinematics data, which can be used as a starting point for the analysis here.

The patient data input platform can then transfer the preliminary implant model, both statically optimized, and tested under the patient specific kinematic envelope, to the dynamic simulation 220, wherein the system can test and refine the preliminary implant model to better suit the patient.

The dynamic simulation 220 can receive data from the patient data input 210 and leverage the patient specific data to refine the preliminary implant model. In the dynamic simulation 220, the kinematic envelope can be applied to the preliminary implant model, and the preliminary implant model can be tested for impingement. For example, in the dynamic simulation 220, the preliminary implant model can change the cup orientation, and run various simulations moving the stem relative the cup. The dynamic simulation 220 can test the preliminary implant model's optimal cup anteversion angle to avoid impingement.

In an example, the dynamic simulation 220 can determine, either through surgeon input, or a record of preferred component positions, the appropriate cup anteversion angle. During testing, the dynamic simulation 220 can measure flexion, extension, abduction, adduction, internal rotation, and external rotation, of the implant model. While measuring these various movements, the dynamic simulation can record and track the cup anteversion and cup inclination. For example, during testing, the cup inclination can be chosen between about 38 and 50 degrees. Cup anteversion can be chosen between about more than 10 degrees. This information can be graphed against each other to determine a corresponding range of motion and appropriate cup positions for the implant model, and be used to determine the appropriate cup anteversion angle for the patient.

The appropriate cup anteversion angle can be used to maximize an impingement free range of motion zone. In an example, a desired cup anteversion angle can be determined, such as at about 25 degrees. Similarly, a desired cup inclination angle can be determined, such as at about 45 degrees. On a plot of cup anteversion against cup inclination, graphical representations of flexion, extension, abduction, adduction, internal rotation, and external rotation can be mapped.

The desired cup anteversion of about 25 degrees and cup inclination of about 45 degrees can serve as the bounds on the graph, and give the surgeon a better idea of what kind and range of motion is within those bounds. For example, a large amount of abduction may be within those bounds, while a smaller amount of internal rotation may be allowed within those bounds. Accordingly, the surgeon can adjust the cup anteversion and cup inclination to allow for the desired range of motion while still maintaining appropriate angles for the implant model.

Once the appropriate cup anteversion angle has been determined, the revised implant model, with static optimization (including appropriate sizing and stem anteversion angle), kinematic optimization (specific to patient desired ROM), and dynamic simulation optimization (with appropriate cup anteversion and impingement free ROM) can be forwarded to the spino-pelvic risk analysis application 230 for determinization of the implant model ROM effect on spine and pelvic kinematics.

At the spino-pelvic risk analysis application 230, the revised preliminary implant model, which has been tested and refined through the dynamic simulation 220, can be tested for spinal and pelvic risk. In the spino-pelvic risk analysis application 230, the produced range of motion can be tested against several literature-based spino-pelvic risks, such as spinal misalignment.

The prescription output application 240 can receive the revised preliminary implant model from the spino-pelvic risk analysis application 230, and determine whether the revised preliminary implant model is ready for use by the surgeon in a preoperative plan, or if further refinement is desired. At the prescription output application 240, if more information is desired, the surgeon can prompt the system to cycle back to any prior step, such as to optimizing patient kinematics.

The prescription output application 240 can be used to determine whether the produced implant model is appropriate. The produced implant model can be provided to the preoperative plan with reasonable confidence in a desired range of motion without impingement. This can allow the surgeon to further inform the patient, and let the patient know what expectation he or she can have for a range of movement after the procedure. Moreover, as the implant modeling is done virtually, the surgeon can have confidence in the implant procedure without having to physically apply an implant. A method of using system 200 is discussed in detail with reference to FIGS. 3A-3B below.

Figure 3A:
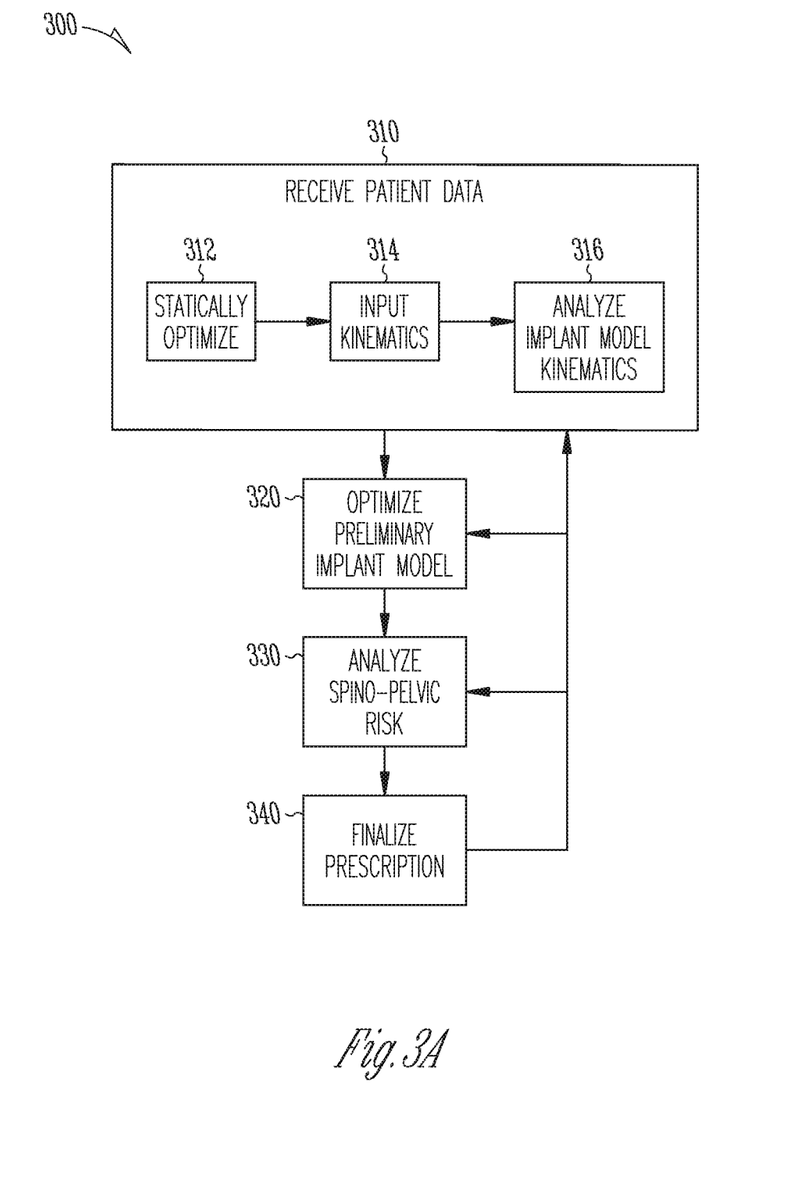
FIG. 3A is a schematic diagram of a method of producing a patient-specific hip implant prescription in an example.
Figure 3B:
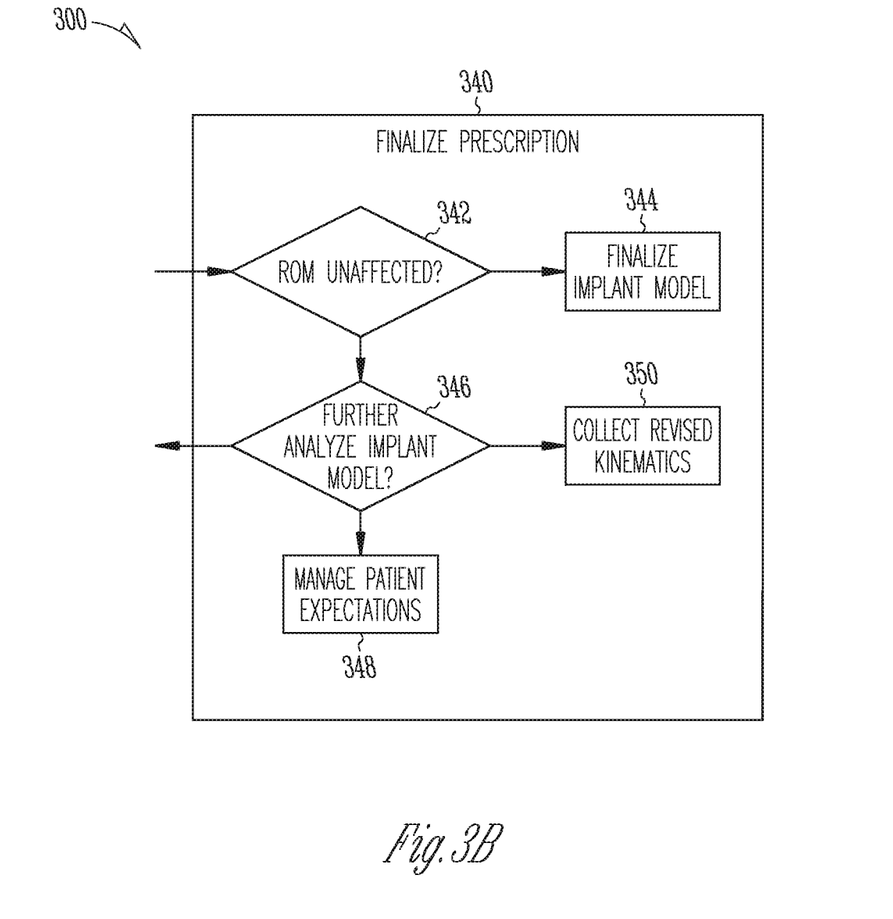
FIG. 3B is a schematic diagram of a method of producing a patient-specific hip implant prescription in an example.

FIGS. 3A and 3B are schematic diagrams of a method 300 of producing a patient-specific hip implant prescription and finalizing a patient-specific hip implant prescription. The method 300 can include receiving patient anatomy data at block 310, statically optimizing the preliminary implant model at block 312, inputting kinematics at block 314, optimizing the preliminary implant model at block 320, analyzing spino-pelvic risk at block 330, and finalizing the prescription at block 340.

The method 300 can, for example, use a system (such as system 200 above) to produce an implant model such as implant model 100 discussed above. The method 300 can generally produce a 3-D implant model for hip replacement, and tailor that model specifically to a patient's anatomy and desired kinematics. The method 300 can include a feedback loop for further refining and personalizing the implant model.

At block 312, patient anatomy is received. For example, CT scans, MRI or x-rays of the patient anatomy around the hip joint can be received. From this information, a three dimensional implant model (such as model 100 discussed above) can be produced. This can produce the generic geometry of the patient's hip joint for use in producing the implant model and preoperative plan.

At block 314, the anatomy data and produced three-dimensional model can be statically optimized. At this point, the size of the cup and stem can be selected based on the anatomy data. The cup placement and stem placement can be determined according to the joint geometry, without additional movement. Statically optimizing the preliminary implant model can include analyzing risk of impingement at both standing and sitting positions. Conventional approaches to implant modeling leveraged static analysis of an implant, such as a hip implant. But many current methods do not go beyond static analysis.

In method 300 at block 316, the preliminary implant model can be analyzed using a larger kinematics envelope personalized to the patient. The range of motion of the implant model (such as model 100 discussed above) can be tested at block 316.

During the kinematics and range of motion analysis at block 316, specific patient desired ranges of motion can be tested on the virtual implant correlating to activities or motions the patient wishes to be able to do post-procedure. For instance, a patient may wish to be able to play a certain sport or walk in a certain manner. This associated activity can have a pre-assigned preferred range of motion for the activity.

With the virtual implant model, a possible range of motion can be determined from an expected interaction between the virtual cup and stem. In some cases, the cup can be articulated relative the stem, and in other cases the stem can be articulated relative to the cup. As the components are moved through the virtual range of motion on the 3-D model, various collisions or impingements can be noted. The collisions can be charted or mapped to determine the limitations of the range of motion of the virtual implant.

In some cases, a range of motion can be determined based on fit analysis. For example, data such as thickness, offset, and placement of each component of the implant can be compared to data from previous models or patients, to determine anticipated range of motion.

In an example analysis, the implant model can be tested using a series of 2-D or 3-D graphs produced to represent the range of motion zones for various functions of the implant, such as hip flexion, extension, hyperextension, and abduction. Each type of motion can be represented by a range of angles. These graphs can be layered on top of one another to show an acceptable range of motion zone that can occur without impingement.

Various daily or recreational activities can be represented a profile within those graphs. For example, a complied range of motion zone acceptable for tennis may include a larger zone for hip flexion, while a comparative range of motion zone for standing would be smaller in hip flexion.

While testing the range of motion of the virtual implant, the range of motion can be displayed, for example, on a user interface such as a monitor or display. In some cases, the range of motion can be a graphical display, such as a graphical representation of a human hip joint. In other cases, a graph or chart can be used to display the boundaries of the range of motion tested on the virtual implant. In some cases, the range of motion can be displayed as a list or table of limits.

Once the range of motion is tested on the virtual implant, the produced range of motion can be compared to the desired range of motion, such as for a specific activity. This comparison can be done internally with the same system, such as by using a lookup table or historical data, or can be done by interaction with an outside system, such as a database of desired ranges of motion for a given activity. In some cases, the user of the system, such as the surgeon, can be prompted to compare the tested range of motion against the desired range of motion for the activity, and determine whether the range of motion is acceptable. In some cases, the user can use the user interface to compare the tested range of motion with the desired range of motion; in this case, the user can enter the decision into the system.

In some cases, the system can compare the produced range of motion to that of a typical healthily hip or to previously recorded information about the patient. In some cases, the system can compare the produced range of motion to that of regular daily activities. In some examples, the system can compare specific aspects of the produced range of motion to one or more pre-determined minimally acceptable ranges or thresholds. In an example, the hip should have an extension range with a minimum of X. The produced range of motion can be compared to this minimum value X.

For example, at block 316, the kinematics of a specific type of hip movement can be tested. A daily activity such as crossing the legs can be tested on the preliminary implant model from block 314. Similarly, a daily activity such as bending downward can be tested on the preliminary implant model from block 314. If the preliminary implant model fails to fall within the desired range of motion, it can be adjusted. Once the system has confirmed that the implant model can accomplish each of these daily activities, and the range of motion of the preliminary implant model is acceptable for each of these daily activities, the implant model can be optimized in a dynamic simulation at block 320.

At block 320, the revised preliminary implant model, to which the kinematics envelope has been applied, can be optimized. At block 320, the optimal cup anteversion angle can be determined to maximize an impingement free range of motion zone for the implant. For example, the cup orientation can be tested and altered as desired so that it allows for the range of motion determined at block 316.

The dynamic optimization of the cup anteversion angle and orientation can begin, for example, at a conventional starting point. The implant model can be virtually tested with the cup anteversion angle and orientation at this starting point. During this testing, the system can simulate the desired range of motion within the implant model with the cup anteversion angle and orientation at this starting point. If, through the full desired range of motion, there are problems, such as potential impingement (e.g., bone on bone), the cup anteversion angle and orientation can be altered a small amount, such as about 0.1 degrees in each direction. The implant model can then be re-tested for the desired range of motion with the adjusted cup anteversion angle and orientation.

Generally, the cup anteversion angle and orientation are limited by a desire to keep the anteversion angle properly within a given clinical and anatomical range. Thus, changes in the anteversion angle and orientation of the cup can be made within that clinical range during the dynamic optimization of the cup anteversion angle and orientation. Nonetheless, a large number of incremental simulations can be run by the system at block 320 to test and adjust the cup anteversion angle and orientation within the desired range of motion.

Additionally, 2-D or 3-D graphical representations of passive motion can be compared to the produced implant model and range of motion zone. The comparison of the graphical data can allow for selection of an appropriate cup anteversion angle that does not cause impingement, with less risk of dislocation.

In some cases, weighting factors can be used during optimization of the implant range of motion and cup anteversion angle and orientation (e.g., at blocks 316 and 320). For example, more weight can be placed on daily activities such as walking, sitting, or bending over. Conversely, less weight can be placed on certain sports, or other preferred, but less essential, recreational activities such as tennis. In this case, the graphical representation of the range of motion zone can highlight or bias the profile within that range of motion zone that applies to the particular activity. During cup optimization, preferential treatment can be applied to the desired profile within the range of motion zone. If weighting is not used, the produced implant model will result in a range of motion in between the profiles of the desired daily and recreational activities.

At block 320, the testing can produce an impingement free range of motion zone associated with the implant model that includes the patient desired, activity-specific ranges of motion. Once the implant model has been optimized for range of motion of daily and recreational activities, and cup anteversion and orientation, the implant model can be tested for spinal and pelvic optimization at block 330. The implant model can be tested based on conventional spino-pelvic risk kinematics.

For example, 2-D or 3-D graphical representations of spino-pelvic risk of a hip joint range of motion can be compared to the produced, optimized implant model of block 320. The spino-pelvic risk can include, for example, an additional set of kinematics data directed to risks associated with the spine and pelvic movement connected to hip joint movements. If the implant model passes the spino-pelvic analysis, and the impingement-free zone produced from block 320 is still acceptable, the implant model can be finalized in block 340. However, if a problem occurs, and the produced implant model has impingement, dislocation, or spino-pelvic risks based on testing, the implant model can be re-tooled and re-tested at block 316, 320, and 330 before being finalized at block 340.

At block 342, once analyzed for spino-pelvic risk, if the impingement free range of motion zone (from block 320) is unaffected, the implant model can be finalized at block 344. If, however, the impingement free range of motion zone (from block 320) should be adjusted due to the spino-pelvic risk analysis (block 330), then the implant model can be further analyzed to determine whether the revised impingement free range of motion zone is clinically acceptable at block 346. If the revised impingement free range of motion zone is clinically acceptable, the implant model can be finalized, with the caveat that patient expectations of range of motion may need to be managed (block 348). If the revised impingement free range of motion zone in not clinically acceptable, revised patient kinematics can be collected (block 350), and the implant model can be re-optimized, starting at block 316. In this way, the method 300 can include a feedback loop to allow for further revision and tailoring of the implant model.

Once the implant model is finalized, with the appropriate impingement free range of motion zone and cup anteversion angle, the implant model can be used to produce a preoperative plan and physical implant. The preoperative plan can include a detailed description of the implant, where the implant should be positioned, and other information such as incision locations, details on disconnection and reattachment of soft tissue, and other appropriate preoperative details.

Patient expectations can also be managed when the preoperative plan is finalized. The surgeon can discuss with the patient realistic expectations for the range of motion of the implant after surgery, and which daily and recreational activities the patient should be able to perform, based on the tested implant model. Method 300 can not only provide an implant selection and orientation, but can also allow for a disclosure to the patient of what his or her movement and ability can be on a day to day basis post-procedure.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods.

The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), memory cards or sticks, random access memories (RAMs), read only memories (ROMs), and the like.

Figure 4:
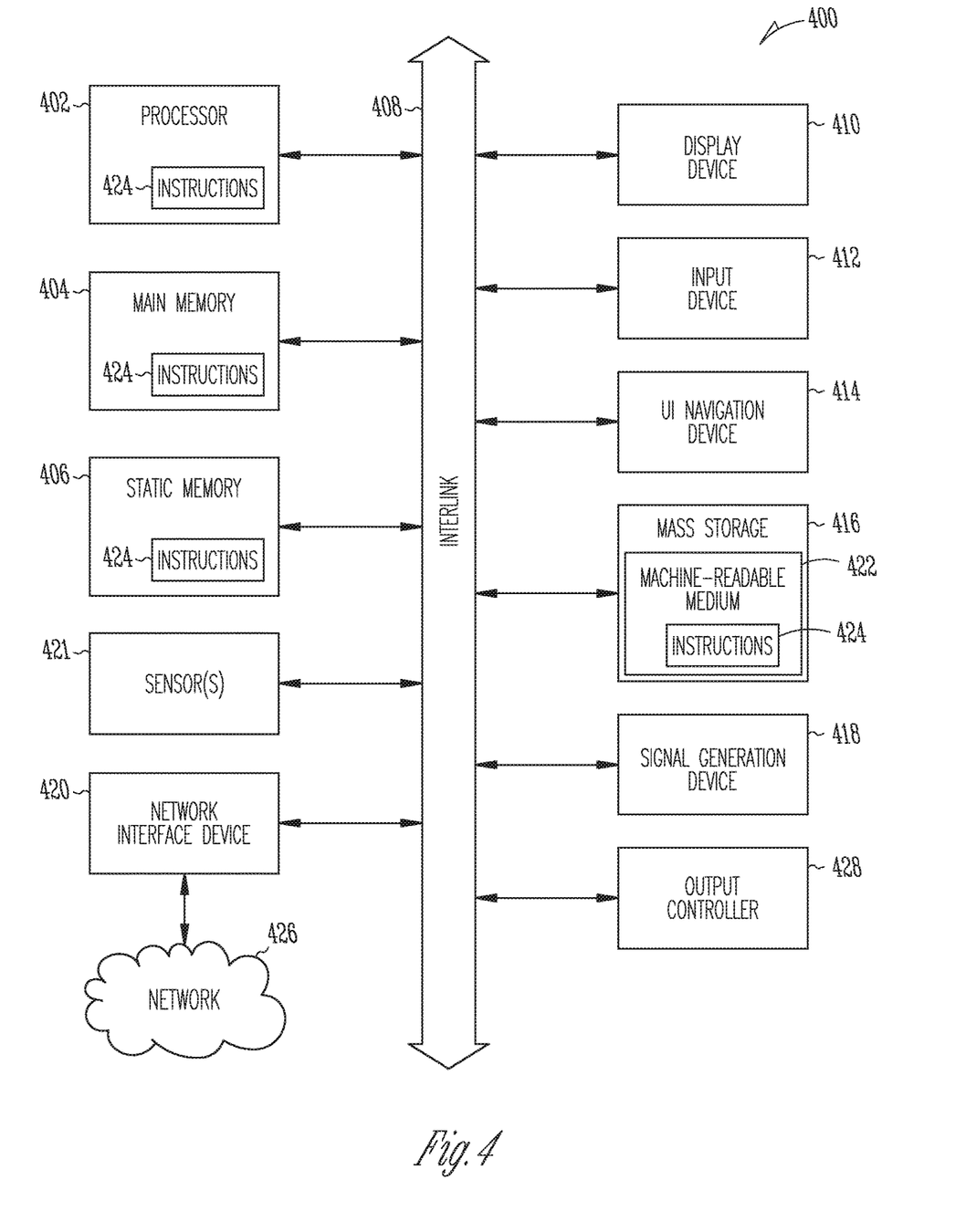
FIG. 4 is a schematic diagram depicting a computer on which a method can be run in an example.

FIG. 4 illustrates schematic showing how system 400 can be connected. System 400 can include local device 401, user interface 402, display 404, interlink 406, central device 408, central device database 410, and expert device 412. Local device 401 can include processor 414, volatile memory 416, static memory 418, and network device 420.

Local device 401 can be any computing device, such as a handheld computer, for example, a smart phone, a tablet, a laptop, a desktop computer, or any other computing device including information processing and storage capabilities and communication capabilities. Local device 401 can include processor 414, volatile memory 416, and static memory, which can be connected by wire or other electrical conduit within local device 401 and can be configured to receive information, process information, output information, and store information. The information can be temporarily stored on volatile memory 416 and can be relatively permanently stored on static memory 418. In some examples, configurations of these components within local device 401 can be considered machine readable medium.

The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

User interface 402 can be any input and/or output device. For example, user interface can be a monitor, keyboard, and mouse in one example. In other examples, user interface 402 can be a touch screen display. Display 404 can be a display for displaying output from local device 401 and in some examples can receive input and transfer input to local device 401 (for example a touch screen display).

Central device 408 can be a remote device similar in configuration to local device 401, but located remotely from local device 401. Central device 408 can be configured to connect to multiple of local devices 401, in some examples, through interlink 406. Similarly, expert device 412 can be a remote device similar in configuration to local device 401, but can be operated by a user considered to be an expert. In operation of some examples, the expert user can interface with the processes and decisions of the methods discussed herein.

In some examples, user interface and display 404 can be connected to local device 401 through wired connections, in some examples (such as USB, for example), and through wireless connections (such as Bluetooth, for example) in other examples. In some other examples, interlink 406 can be a local area network (LAN), wide area network (WAN), and internet protocol (TCP/IP) connections. Local device 401 can be similarly connected to interlink 406 (either through a wired or wireless connection). In some examples, network device 420 can connect local device 401 to interlink 406. Central device 408, central device database 410, and expert device 412 can be connected to interlink 406 in a similar manner.

In operation of some examples, system 400 can be configured to perform steps of the methods discussed herein and, in some examples, may perform steps based on a program stored in volatile memory 416 or static memory 418, where results of the analysis are stored in either volatile memory 416 and/or static memory 418 can be displayed on display 404 and/or transmitted to user interface 402, central device 408, central device database 410, and/or expert device 412. For example, system 400 can develop a reverse shoulder arthroplasty plan by receiving an image of a patient shoulder. One of local device 401, central device 408, and expert device 412 can segmented the image to develop a 3D shoulder model.

Then, a device (such as local device 401) can perform virtual surgery on the 3D shoulder model to generate a modified shoulder model. The modified shoulder model can be stored in volatile memory 416 and/or static memory 418. In some examples, the virtual surgery can include resecting and reaming a virtual humerus of the 3D shoulder model, and reaming a virtual glenoid of the 3D shoulder model, which can be displayed for example, on display 404. Thereafter, selection of a humeral implant and selection of a glenoid implant can be received from a user interface, such as user interface 402, in some examples, and can be made by local device in some other examples.

Local device 401, central device 408, or expert device 410 can implant a virtual representation of the humeral implant on the virtual humerus and can implant a virtual representation of the glenoid implant on the virtual glenoid to virtually update the modified shoulder model. The updated modified shoulder model can be stored in volatile memory 416 and/or static memory 418. In some examples, the updated modified shoulder model can be stored in central device 408 or expert device 412. One of local device 401, central device 408, and expert device 410 can then determine a range of motion of the patient shoulder and a reverse shoulder arthroplasty can be finalized based on the range of motion.

Similarly, system 400 can be configured to perform steps of each method discussed herein.

VARIOUS NOTES & EXAMPLES

Example 1 can include a method for producing an implant model, the method comprising: receiving patient specific data comprising patient anatomy information and patient specific kinematics; producing a preliminary implant model based on the received patient specific data; running, using processing circuitry, a simulation on the preliminary implant model to produce a revised implant model with a range of motion zone using the patient specific kinematics; optimizing the preliminary implant model with a dynamic simulation to determine a cup anteversion angle and a revised impingement free range of motion zone; analyzing the revised implant model for spino-pelvic risk using spino-pelvic kinematics, and adjusting the implant model based on the spino-pelvic risk; and outputting the implant model for display on a user interface.

Example 2 can include Example 1, wherein the patient specific kinematics comprise desired range of motion, average kinematics for tasks at high risk of dislocation, kinematics for desired daily activity, kinematics for desired recreational activity, or combinations thereof.

Example 3 can include any of Examples 1-2, wherein receiving patient anatomy information comprises receiving images of the patient's anatomy.

Example 4 can include any of Examples 1-3, further comprising outputting a three-dimensional model of the patient anatomy based on the patient anatomy information.

Example 5 can include any of Examples 1-4, wherein producing a preliminary implant model comprises selecting a stem and cup size based on the patient anatomy information.

Example 6 can include any of Examples 1-5, wherein producing a preliminary implant model comprises statically optimizing the preliminary implant model.

Example 7 can include any of Examples 1-6, wherein the patient specific kinematics comprise range of motion envelopes for one or more daily or recreational activities for the implant model.

Example 8 can include any of Examples 1-7, wherein the patient specific kinematics comprise average kinematics for daily and recreational activities based on a patient profile.

Example 9 can include any of Examples 1-8, wherein running a simulation on the preliminary implant model comprises testing a range of motion of the implant and comparing the range of motion to a desired range of motion.

Example 10 can include any of Examples 1-9, wherein optimizing the preliminary implant model with a dynamic simulation comprises testing range of motion of the implant model with various cup configurations.

Example 11 can include any of Examples 1-10, wherein optimizing the preliminary implant model with a dynamic simulation comprises determining an impingement free range of motion zone for the implant model.

Example 12 can include any of Examples 1-11, wherein analyzing spino-pelvic risk comprises applying average spino-pelvic kinetics models to the preliminary implant model.

Example 13 can include any of Examples 1-12, further comprising testing the implant model within a clinically accepted range of motion.

Example 14 can include any of Examples 1-13, further comprising producing a treatment plan for the patient including the implant model.

Example 15 can include a method for providing implant parameter data, the method comprising: receiving patient specific data comprising patient anatomy information and patient kinematics; determining an implant size and a stem anteversion angle based on the patient anatomy information; producing a range of motion for the patient based on the determined implant size and the patient kinematics, wherein the range of motion is impingement free; constructing a preliminary implant model based on the range of motion; analyzing spino-pelvic risk of damage due to the preliminary implant model and revising the preliminary implant model based on the spino-pelvic risk; and outputting the revised preliminary implant model for display on a user interface.

Example 16 can include Example 15, further comprising producing a treatment recommendation for the patient based on the revised preliminary implant model.

Example 17 can include any of Examples 15-16, further comprising managing patient expectations based on the revised preliminary implant model.

Example 18 can include a system comprising: processing circuitry; and memory, the memory including instructions for producing an implant model, which when executed by the processing circuitry, causes the processing circuitry to: receive patient specific data comprising patient anatomy information and patient specific kinematics; produce a preliminary implant model based on the received patient specific data; run a simulation on the preliminary implant model to produce a revised implant model with a range of motion zone using the patient specific kinematics; optimize the preliminary implant model with a dynamic simulation to determine a cup anteversion angle and a revised impingement free range of motion zone; analyze the revised implant model for spino-pelvic risk using spino-pelvic kinematics, and adjusting the implant model based on the spino-pelvic risk; and output the implant model for display on a user interface.

Example 19 can include Example 18, wherein the patient specific kinematics comprise desired range of motion, average kinematics for tasks at high risk of dislocation, kinematics for desired daily activity, kinematics for desired recreational activity, or combinations thereof.

Example 20 can include any of Examples 18-19, further comprising instructions to produce a patient treatment plan including the range of motion zone.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for producing an implant model, the method comprising:
  receiving patient specific data comprising patient anatomy information and patient specific kinematics;
  producing a preliminary implant model based on the received patient specific data;

running, using processing circuitry, a simulation on the preliminary implant model to produce a revised implant model with a range of motion zone using the patient specific kinematics;

optimizing the preliminary implant model with a dynamic simulation to determine a cup anteversion angle and a revised range of motion zone which is impingement free;

analyzing the revised implant model for spino-pelvic risk using spino-pelvic kinematics, and adjusting the revised implant model based on the spino-pelvic risk; and outputting the revised implant model for display on a user interface.

2. The method of claim 1, wherein the patient specific kinematics comprise desired range of motion, average kinematics for tasks at high risk of dislocation, kinematics for desired daily activity, kinematics for desired recreational activity, or combinations thereof.

3. The method of claim 1, wherein receiving patient anatomy information comprises receiving images of the patient's anatomy.

4. The method of claim 1, further comprising outputting a three-dimensional model of the patient anatomy based on the patient anatomy information.

5. The method of claim 1, wherein producing the preliminary implant model comprises selecting a stem and cup size based on the patient anatomy information.

6. The method of claim 5, wherein producing the preliminary implant model comprises statically optimizing the preliminary implant model.

7. The method of claim 1, wherein the patient specific kinematics comprise range of motion envelopes for one or more daily or recreational activities for the implant model.

8. The method of claim 1, wherein the patient specific kinematics comprise average kinematics for daily and recreational activities based on a patient profile.

9. The method of claim 1, wherein running a simulation on the preliminary implant model comprises testing the range of motion zone of the implant model and comparing the range of motion zone of the implant model to a desired range of motion zone of the implant model.

10. The method of claim 1, wherein optimizing the preliminary implant model with a dynamic simulation comprises testing range of motion of the implant model with various cup configurations.

11. The method of claim 1, wherein optimizing the preliminary implant model with a dynamic simulation comprises determining an impingement free range of motion zone for the implant model.

12. The method of claim 1, wherein analyzing spino-pelvic risk comprises applying average spino-pelvic kinetics models to the preliminary implant model.

13. The method of claim 1, further comprising testing the implant model within a clinically accepted range of motion zone.

14. The method of claim 1, further comprising producing a treatment plan for a patient including the implant model.

15. A method for providing implant parameter data for a patient, the method comprising:
receiving patient specific data comprising patient anatomy information and patient kinematics;
determining an implant size and a stem anteversion angle based on the patient anatomy information;
producing a range of motion zone for the patient based on the determined implant size and the patient kinematics, wherein the range of motion zone is impingement free;
constructing a preliminary implant model based on the range of motion zone;
analyzing spino-pelvic risk of damage due to the preliminary implant model and revising the preliminary implant model based on the spino-pelvic risk; and
outputting the revised preliminary implant model for display on a user interface.

16. The method of claim 15, further comprising producing a treatment recommendation for the patient based on the revised preliminary implant model.

17. The method of claim 15, further comprising managing patient expectations based on the revised preliminary implant model.

18. A system comprising:
processing circuitry; and
memory, the memory including instructions for producing an implant model, which when executed by the processing circuitry, causes the processing circuitry to:
receive patient specific data comprising patient anatomy information and patient specific kinematics;
produce a preliminary implant model based on the received patient specific data;
run a simulation on the preliminary implant model to produce a revised implant model with a range of motion zone using the patient specific kinematics;
optimize the preliminary implant model with a dynamic simulation to determine a cup anteversion angle and a revised range of motion zone which is impingement free;
analyze the revised implant model for spino-pelvic risk using spino-pelvic kinematics, and adjusting the revised implant model based on the spino-pelvic risk; and
output the revised implant model for display on a user interface.

19. The system of claim 18, wherein the patient specific kinematics comprise desired range of motion zone, average kinematics for tasks at high risk of dislocation, kinematics for desired daily activity, kinematics for desired recreational activity, or combinations thereof.

20. The system of claim 18, further comprising instructions to produce a patient treatment plan including the range of motion zone.

* * * * *